(12) United States Patent
Bayon et al.

(10) Patent No.: US 8,834,578 B2
(45) Date of Patent: *Sep. 16, 2014

(54) BIORESORBABLE IMPLANT

(75) Inventors: Yves Bayon, Lyons (FR); Philippe Gravagna, Irigny (FR); Alfredo Meneghin, Lyons (FR); Michel Therin, Lyons (FR)

(73) Assignee: Sofradim Production (FR)

( * ) Notice: Subject to any disclaimer, the term of this patent is extended or adjusted under 35 U.S.C. 154(b) by 1468 days.

This patent is subject to a terminal disclaimer.

(21) Appl. No.: 11/881,838

(22) Filed: Jul. 30, 2007

(65) Prior Publication Data

US 2009/0036997 A1 Feb. 5, 2009

(51) Int. Cl.
| | |
|---|---|
| *A61F 2/02* | (2006.01) |
| *A61L 27/58* | (2006.01) |
| *A61L 27/38* | (2006.01) |
| *A61L 31/00* | (2006.01) |
| *D04B 21/12* | (2006.01) |
| *A61L 31/14* | (2006.01) |
| *A61L 31/12* | (2006.01) |
| *A61L 27/48* | (2006.01) |
| *A61L 27/56* | (2006.01) |

(52) U.S. Cl.
CPC ........... *A61L 31/146* (2013.01); *A61L 27/58* (2013.01); *D10B 2403/0213* (2013.01); *A61L 27/38* (2013.01); *D10B 2403/0112* (2013.01); *A61L 31/005* (2013.01); *D04B 21/12* (2013.01); *D10B 2509/08* (2013.01); *A61L 31/148* (2013.01); *A61L 31/129* (2013.01); *A61L 27/48* (2013.01); *A61L 27/56* (2013.01)
USPC ...................................... 623/23.75

(58) Field of Classification Search
USPC ....................................... 623/23.75
See application file for complete search history.

(56) References Cited

U.S. PATENT DOCUMENTS

| | | | | |
|---|---|---|---|---|
| 4,970,298 | A | * 11/1990 | Silver et al. | ............... 530/356 |
| 5,891,558 | A | * 4/1999 | Bell et al. | .................. 428/218 |
| 6,153,292 | A | 11/2000 | Bell et al. | |
| 6,262,332 | B1 | 7/2001 | Ketharanathan | |
| 6,264,702 | B1 | * 7/2001 | Ory et al. | ............... 623/23.75 |
| 6,391,939 | B2 | 5/2002 | Tayot et al. | |
| 6,443,964 | B1 | 9/2002 | Ory et al. | |
| 6,451,032 | B1 | * 9/2002 | Ory et al. | .................. 606/151 |
| 6,576,019 | B1 | 6/2003 | Atala | |
| 6,596,304 | B1 | 7/2003 | Bayon et al. | |

(Continued)

FOREIGN PATENT DOCUMENTS

| | | |
|---|---|---|
| EP | 0999805 | 5/2000 |
| EP | 1 216 717 | 6/2002 |

(Continued)

OTHER PUBLICATIONS

Gunatillake, et al., Eur. Cells and Mat., vol. 5, 2003.*

(Continued)

*Primary Examiner* — Susan Tran
*Assistant Examiner* — William Craigo

(57) ABSTRACT

Bioresorbable wall reinforcement implants include a bioresorbable porous matrix based on a collagen sponge which defines first pores, a bioresorbable porous three-dimensional knit which defines second pores, with the matrix filling the knit and all the first and second pores being at least partially interconnected with one another. Tissue engineering supports including such an implant and uses thereof are also described.

36 Claims, 6 Drawing Sheets

(56) References Cited

U.S. PATENT DOCUMENTS

| | | | |
|---|---|---|---|
| 6,599,323 B2 * | 7/2003 | Melican et al. | 623/23.72 |
| 6,790,454 B1 | 9/2004 | Abdul Malak et al. | |
| 6,974,679 B2 | 12/2005 | Andre et al. | |
| 2002/0120291 A1 * | 8/2002 | Shalaby | 606/230 |
| 2003/0119985 A1 * | 6/2003 | Sehl et al. | 525/54.1 |
| 2003/0225355 A1 | 12/2003 | Butler | |
| 2004/0054376 A1 * | 3/2004 | Ory et al. | 606/151 |
| 2004/0132365 A1 | 7/2004 | Therin | |
| 2006/0286144 A1 * | 12/2006 | Yang et al. | 424/426 |
| 2007/0032805 A1 | 2/2007 | Therin | |

FOREIGN PATENT DOCUMENTS

| | | | |
|---|---|---|---|
| EP | 1 216 718 | 6/2002 | |
| EP | 1216718 A1 * | 6/2002 | A61L 27/58 |
| EP | 1 273 312 | 1/2003 | |
| EP | 1 535 631 | 6/2005 | |
| JP | 11 319068 | 11/1999 | |
| WO | WO 89/08467 | 9/1989 | |
| WO | WO 96/08277 | 3/1996 | |
| WO | WO99/16381 * | 9/1998 | A61F 2/00 |
| WO | WO 99/06079 | 2/1999 | |
| WO | WO 00/16821 | 3/2000 | |
| WO | WO 99/05990 | 5/2000 | |
| WO | WO 2006/138098 | 12/2006 | |

OTHER PUBLICATIONS

Chen, et al., Chem. Comm., Jul. 19, 2000.*

Laquerriere, J. Neurosurg., 78, 1993.*

Friess, Eur. J. Pharm. Biopharm., 45, 1998.*

International Search Report from PCT/IB/2008/002989 dated Nov. 23, 2009.

A. Hunt et al., Abstract Book, Tissue Engineering & Regenerative Medicine, International Society, European Chapter Meeting 2006, Rotterdam, The Netherlands, Oct. 8-11, 2006, p. 130.

O. LeFranc et al., Urothelial Cell Proliferation on Novel 3D Collagent-PLLA Composites for Urological Tissue Engineering, 1 page, 2006.

O. LeFranc, Enhancement of Smooth Muscle Cell Proliferation in Novel PLLA-Collagent Meshes for Tissue Engineering, 1 page, 2006.

* cited by examiner

B5 B6

B2 B1

B4 B3

B4 B3

BIORESORBABLE IMPLANT

TECHNICAL FIELD

The present disclosure relates to a bioresorbable wall reinforcement implant that can be used, for example, in the treatment of hernias or for the reconstruction of a wall, for example a visceral wall, when a permanent implant is not necessary. The implants according to the present disclosure can also be used in vitro as a tissue engineering product or support for culturing live cells.

BACKGROUND

A hernia causes a defect in a wall of the human body, for example in the abdominal wall. Various other phenomena can create various faults, i.e. a lack of tissue, in various walls of the human body, for instance the visceral walls (intestine, stomach, uterus, bladder, urethra, ureter, etc.) and the abdominal wall.

In order to treat the drawbacks associated with these phenomena, wall reinforcement implants have been developed, for example, based on a biocompatible textile which is implanted at the defect in order to overcome a lack of tissue. These implants are often permanent.

In order to limit the introduction of synthetic foreign bodies into the human body, implants have also been developed which are based on products obtained from porcine dermis or from a human cadaver, which are decellularized and then implanted at the wall defect. However, although these products are washed, they can cause necroses and death of the neighbouring tissues.

However, in certain cases, permanent implants are not necessary. Moreover, as indicated above, in the case of the treatment of these defects, one seeks to limit the amount of foreign bodies called upon to remain permanently in a human body and to promote tissue reconstruction.

Thus, the structure of the implant may be favourable to cell growth. At the same time, the implant must exhibit a minimum amount of mechanical strength in order to perform its reinforcement function. In particular, when the implant is bioresorbable, it is important for the cell colonization to take place gradually and in a controlled manner, and at the same time in a homogeneous manner, as the implant degrades.

Bioresorbable wall reinforcement implants already exist.

Thus, document US2003/0225355 discloses an implant based on a bioresorbable collagen matrix that can trap a two-dimensional textile that may be bioresorbable. However, such an implant does not allow satisfactory cell growth. In particular, such an implant does not allow gradual, controlled and homogeneous cell colonization of the textile.

Document EP 1 216 718 discloses an implant including a bioresorbable polymeric sponge reinforced with a two-dimensional textile. However, such an implant does not allow satisfactory cell growth either. In particular, such an implant does not allow gradual, controlled and homogeneous cell colonization of the textile.

U.S. Pat. No. 6,262,332 discloses a biomaterial including a layer of nonhuman collagen and a two-dimensional textile. However, such an implant does not allow satisfactory cell growth. In particular, such an implant does not allow gradual, controlled and homogeneous cell colonization of the textile.

Thus, there remains the need for an entirely bioresorbable implant which has sufficient mechanical properties while at the same time allowing effective, gradual and controlled cell growth, so that the tissue regeneration is accomplished effectively during the time the implant is effectively present in the human body, i.e. before bioresorption of the implant.

SUMMARY

The present disclosure aims to remedy this need by providing a bioresorbable wall reinforcement implant, that includes at least a bioresorbable porous matrix based on a collagen sponge which defines first pores and a bioresorbable porous three-dimensional knit which defines second pores with the first and second pores being at least partially interconnected with one another and porous matrix filling the three-dimensional knit.

In the present application, the term "implant" is intended to mean a biocompatible medical device that can be implanted in the human or animal body.

In the present application, the term "bioresorbable" is intended to mean the characteristic according to which an implant and/or a material is absorbed by the biological tissues and disappears in vivo after a given period of time, that may vary, for example, from one day to several months, depending on the chemical nature of the implant and/or of the material.

For the purpose of the present application, the term "porous" is intended to mean the characteristic according to which a structure exhibits pores, or alternatively gaps, alveoli, holes or orifices, which are open, which may or may not be evenly distributed, and which promote all cell colonization.

For the purpose of the present application, the term "sponge" is intended to mean a porous structure with pores which may or may not be interconnected, obtained, for example, by lyophilization of a solution or suspension.

For the purpose of the present application, the term "collagen" is intended to mean any known collagen of porcine, bovine or human origin, for example natural collagen, esterified collagen, for example methylated, ethylated or alternatively succinylated collagen, or one of its derivatives, which may or may not be heated, which may or may not be oxidized, or alternatively, for example, which is crosslinked with another compound.

For the purpose of the present application, the term "natural collagen" is intended to mean collagen which has not been chemically modified, other than a possible treatment with pepsin in order to digest the telomeric peptides.

For the purpose of the present application, the term "three-dimensional knit" is intended to mean an assembly or arrangement of monofilament or multifilament yarns, obtained by knitting and having a significant thickness, in embodiments of greater than or equal to 0.5 mm. The yarns of the three-dimensional knit of the present disclosure are biocompatible.

For the purpose of the present application, the term "interconnected pores" is intended to mean open pores which are connected to one another and communicate with one another over the implant as a whole, without partitioning, such that a cell that is in a pore can pass from one pore to the other, over the entire implant, and can in theory circulate through all the pores of the implant. For the purpose of the present application, the expression "pores which are at least partially interconnected" is intended to mean that certain pores, for example from 0.1% to 80% of all the pores, may be closed and not communicate with the adjacent pores. In its initial state, before implantation, the implant according to the present disclosure may be such that all of its pores, i.e. the first and the second pores, are all completely interconnected. In another embodiment of the present disclosure, the implant may be such that, in its initial state, before implantation, all of its pores, i.e. the first and the second pores, are partially interconnected, i.e. certain pores are closed to communication with the adjacent pores. In such a case, the gradual degradation in vivo of the various elements constituting the implant, and in particular of the collagen sponge, allows the pores that were initially closed, to be opened little by little. After sufficient partial degradation in vivo after implantation, all the pores, the first and the second pores, become completely interconnected.

For the purpose of the present application, the term "interconnectivity" is intended to mean the ability of the implant to allow any cell that is in a pore to circulate within all the other pores of the implant. Thus, in the case of complete interconnectivity, all the pores of the implant are accessible to any cell originating from the organism into which the implant is implanted.

The implant according to the present disclosure is particularly suitable for the treatment of wall defects and for tissue reconstruction when a permanent reinforcement is not necessary. In fact, due to its three-dimensional bioresorbable porous structure in which all the pores are interconnected, the implant according to the present disclosure promotes a gradual, controlled and homogeneous cell growth. Thus, as each element of the implant, i.e. the collagen sponge matrix and the knit trapped within this matrix, degrades in vivo, the cells proliferate and regenerate the tissue at the site of the defective wall. The more the regenerated tissue grows, the more the mechanical strength of the implant decreases, subsequent to its gradual degradation. In addition, the cells can circulate in all the sites of the implant by virtue of the interconnectivity of the pores of the sponge matrix and of the pores of the three-dimensional knit: thus, the cell growth is evenly distributed over the entire implant, leaving, once the implant is completely resorbed, a tissue reconstructed at the site where the implant was initially implanted, i.e. at the site of the original tissue defect.

In one embodiment of the implant of the present disclosure, the collagen is a mixture of at least one collagen which undergoes slow bioresorption in vivo and at least one collagen which undergoes rapid bioresorption in vivo.

The expression "collagen which undergoes slow bioresorption or bio-degradation in vivo" is intended to mean a collagen that can be completely bioresorbed or degraded in vivo, i.e. within the human body, according to an adaptable and controllable time period ranging from approximately 3 months to 12 months. The expression "collagen which undergoes rapid bioresorption or biodegradation in vivo" is intended to mean a collagen which can be completely bioresorbed or degraded in vivo, i.e. within the human body, according to an adaptable and controllable time period ranging from approximately 1 week to 8 weeks.

In embodiments of the present disclosure, the collagen sponge matrix may exhibit, once implanted, two-speed resorption kinetics, with a part of its structure which resorbs more rapidly than the other part. Such an embodiment thus makes it possible to create, in a gradual and controlled manner, new pores that are interconnected with the already existing pores, that the cells will colonize little by little as the part made of collagen which undergoes rapid bioresorption is degraded. The cell growth will thus gradually take place homogeneously. Such an embodiment also makes it possible to increase the interconnectivity of the implant over time and thus improve the tissue integration of the implant.

The collagen which undergoes slow bioresorption in vivo can be chosen from natural collagen, esterified collagen, which may or may not be heated, and mixtures thereof, and more particularly chosen from the group including glutaraldehyde-crosslinked collagen, bifunctional or trifunctional glycidyl ethers, carbodiimides, acyl azides, divinylsulphone and mixtures thereof. It may also be obtained by crosslinking the collagen by means of physical methods such as photooxidation.

The collagen which undergoes rapid bioresorption in vivo may be chosen from natural collagen, esterified collagen, which may or may not be heated, and mixtures thereof, and more particularly chosen from oxidized collagen, glutaraldehyde-crosslinked collagen, bifunctional or trifunctional glycidyl ethers, carbodiimides, acyl azides, divinylsulphone, collagen crosslinked by UV irradiation or by heat treatment, and mixtures thereof.

In one embodiment of the present disclosure, the collagen forming the sponge is a mixture of oxidized collagen and glutaraldehyde-crosslinked collagen. It is known that oxidized collagen degrades in vivo and is bioresorbed in a few weeks, whereas glutaraldehyde-crosslinked collagen bioresorbs in several months. Thus, the degradation of the oxidized collagen creates, within the sponge matrix of the implant according to the present disclosure, new first pores, interconnected with the second pores of the knit, and the cell growth can spread out in a homogeneous, gradual and controlled manner, and can little by little invade the space left free by the degradation of the oxidized collagen. However, during the degradation of the oxidized collagen, the implant maintains sufficient mechanical strength due to the presence both of the glutaraldehyde-crosslinked collagen which itself degrades less rapidly than the oxidized collagen, and of the three-dimensional knit.

In one embodiment of the present disclosure, the three-dimensional knit consists of monofilament and/or multifilament yarns made of bioresorbable material which has an in vivo degradation time ranging from approximately 3 months to 2 years.

Thus, as the collagen forming the matrix sponge of the implant according to the present disclosure degrades, the implant maintains its mechanical strength due to the knit, which degrades more slowly than the collagen or the mixture of collagen forming the matrix sponge of the implant according to the present disclosure.

In one embodiment of the implant of the present disclosure, the bioresorbable material may be chosen from poly(lactic acid) (PLA), poly(glycolic acid) (PGA), oxidized cellulose, polycaprolactone (PCL), polydiaxanone (PDO), trimethylene carbonate (TMC), polyvinyl alcohol (PVA), polyhydroxyalkanoates (PHAs), polyamides, polyethers, copolymers thereof and mixtures thereof.

In one embodiment of the implant of the present disclosure, the second pores have an average diameter ranging from 1 to 5 mm.

In one embodiment of the implant of the present disclosure, the knit has a two-dimensional porosity of less than or equal to 20%.

For the purpose of the present application, the term "two-dimensional porosity" is intended to mean a porosity calculated from two-dimensional images corresponding to views from above the implant according to the present disclosure, these images then being processed by software which analyses them, for instance the Image J software.

In one embodiment of the present disclosure, the knit has a three-dimensional porosity of greater than or equal to 90%.

For the purpose of the present application, the term "three-dimensional porosity" is intended to mean a porosity measured in the following way: the dimensions, i.e. length, width and thickness, of the knit, taken alone, are measured; moreover, the density of the yarns used to knit this knit are known. The knit is weighed. By means of a simple subtraction, the volume occupied by the empty spaces within the knit is deduced therefrom. The three-dimensional porosity over the entire knit is determined as being the percentage of empty volume relative to the total volume of the knit.

Thus, in embodiments, the knit of the implant according to the present disclosure has both a two-dimensional porosity of less than or equal to 20% and a three-dimensional porosity of greater than or equal to 90%. The combination of these porosity values, which may appear to be paradoxical, makes it possible in particular to obtain, with the sponge forming the matrix of the implant according to the present disclosure, an interconnectivity for excellent cell growth. Thus, when the implant according to the present disclosure is manufactured, the collagen forming the sponge of the implant matrix has, by virtue of the high three-dimensional porosity of the knit of the implant according to the present disclosure, a direct access within the three-dimensional structure and therefore the pores of the knit. Moreover, the three-dimensional porosity of the knit of the implant according to the present disclosure also makes it possible to limit as much as possible the mass of textile in the implant according to the present disclosure, and therefore the mass of foreign body when it is implanted.

Furthermore, it is also advantageous for the knit of the implant according to the present disclosure to have a relatively low two-dimensional porosity, in embodiments less than or equal to 20%, in order to maintain in the knit and therefore in the implant according to the present disclosure, mechanical properties that are appropriate for the function that it is called upon to perform, i.e. reinforce a defective wall, in particular sufficient mechanical strength. The applicant has also noted that such a dimensional porosity of the three-dimensional knit contributes to forming interconnected pores in the collagen sponge, in all the dimensions of the sponge. Thus, the degree of interconnectivity of the pores of the collagen sponge, i.e. of the first pores, can also be controlled, to a certain extent, by the two-dimensional porosity of the three-dimensional knit, which can be made to vary between 0 and 20%.

In one embodiment of the implant of the present disclosure, the three-dimensional knit has a thickness ranging from approximately 2 mm to 6 mm, in embodiments ranging from 2 mm to 4 mm.

The thickness of the three-dimensional knit defines the space in which the regeneration of the defective wall will take place. It is thus determined by the thickness of the wall to be regenerated. In embodiments, it is equivalent to the thickness of the wall to be regenerated.

In one embodiment of the present disclosure, the three-dimensional knit includes a first face and a second face, the first face and the second face being opposite and separated from one another by the thickness of the knit, the first face and the second face being connected to one another by a spacer made of monofilament yarns, multifilament yarns or a combination of monofilament yarns and multifilament yarns.

In the present application, the term "spacer" is intended to mean the sheet(s) of yarns which connect(s) the two faces of a three-dimensional fabric to one another, thus constituting the thickness of such a knit.

Such an embodiment of the knit of the implant according to the present disclosure, with spacer yarns connecting a first face of the knit to a second face of the knit, contributes to reinforcing the interconnectivity of the pores, and in particular of the first pores, throughout the thickness of the collagen sponge, included in the three-dimensional knit. The interconnectivity of these pores can also be controlled, to a certain extent, by the density of the spacer yarns and their distribution between the two faces of the three-dimensional knit.

In one embodiment of the present disclosure, the spacer is made of monofilament yarns.

Such an embodiment of the knit of the implant according to the present disclosure, with the spacer made of monofilament yarns, makes it possible to confer excellent mechanical strength on the knit and thus the implant according to the present disclosure. In particular, during the optional step of thermosetting the knit, the latter keeps its mechanical properties intact. The implant can thus be handled extremely easily by the surgeon. Moreover, such an implant effectively performs its wall reinforcement functions throughout the entire period required for cell colonization in order to regenerate the tissue at the site of the original tissue defect and in the three-dimensional space provided by the knit.

The first and second faces of the knit can be made of monofilament yarns, multifilament yarns or a combination of monofilament and multifilament yarns.

The monofilament or multifilament yarns used to prepare the first and second faces and the spacer of the three-dimensional knit of the implant according to the present disclosure can be chosen from yarns made of material which undergoes slow bioresorption, yarns made of material which undergoes rapid bioresorption, and mixtures thereof.

The expression "yarn made of material which undergoes slow bioresorption" is intended to mean yarn obtained from a material that can be completely bioresorbed or degraded in vivo, i.e. within the human body, according to an adaptable and controllable period of time ranging from approximately 6 months to 2 years.

As an example of a yarn made of material which undergoes slow bioresorption, mention may be made of poly(lactic acid) yarns.

The expression "yarn made of material which undergoes rapid bioresorption" is intended to mean a yarn obtained from a material that can be completely bioresorbed or degraded in vivo, i.e. within the human body, according to an adaptable and controllable period of time ranging from approximately 1 week to 6 months.

As examples of yarns made of material which undergoes rapid bioresorption, mention may be made of poly(glycolic acid) yarns, oxidized cellulose yarns, poly(lactic acid) yarns partially degraded by a treatment such as repeat cycles of gamma-irradiation at doses of greater than or equal to 25 kGy, and mixtures thereof.

In one embodiment of the present disclosure, the monofilament yarns which make up the spacer can consist of yarns made of material which undergoes slow bioresoprtion, for example of poly(lactic acid). The first and second faces can also be made of a mixture of multifilament yarns made of material which undergoes slow bioresorption, for instance poly(lactic acid), and of multifilament yarns made of material which undergoes rapid bioresorption, for instance of poly (glycolic acid) or oxidized cellulose.

In another embodiment of the implant according to the present disclosure, the monofilament yarns which make up the spacer can, for example, include a mixture of yarns which undergo slow bioresorption and yarns which undergo rapid bioresorption. The first and second faces can be made of a mixture of multifilament yarns made of material which undergoes slow bioresorption, for example poly(lactic acid) and of multifilament yarns made of material which undergoes rapid bioresorption, for instance of poly(glycolic acid) or oxidized cellulose.

In one embodiment of the implant according to the present disclosure, the knit is isoelastic.

For the purpose of the present application, the term "isoelastic knit" is intended to mean a knit which has isotropic elastic mechanical properties, i.e. substantially equivalent in all directions.

In embodiments, the ratio of respective extensions in the warp direction and in the weft direction of the knit of the implant according to the present disclosure is between 0.4 and 2.5, at a physiological force of for example 50 N for abdominal wall repair.

It has been found that an isoelastic knit allows excellent reinforcement of visceral walls: specifically, the knit is deformed and extended in a more homogeneous manner, thus limiting the risk of wall or hernia rupture.

In one embodiment of the implant of the present disclosure, at least a part of the yarns constituting the three-dimensional knit are coated with a bioresorbable coating. For example, the coating can be chosen from collagen, chitosan, polysaccharides or mixtures thereof. The polysaccharides can be chosen from hyaluronic acid, alginic acid, polyglucuronic acid, chitosan, starch, soluble cellulose derivatives, and mixtures thereof. Such a yarn coating makes it possible in particular to eliminate any possible crevice within the knit of the implant according to the present disclosure, for example where the yarns cross each other, such crevices being liable to create sites where bacteria or inflammatory cells develop. Such an implant thus makes it possible to reduce the risks of inflammation and sepsis, the bioresorbable coating making the accessible surface of the knit completely smooth and thus preventing the installation of undesirable bacteria and/or microorganisms and/or inflammatory cells.

In one embodiment of the present disclosure, the implant also includes one or more active compounds for improving wall and tissue repair. Suitable active ingredients include, but are not limited to antiseptics, anti-inflammatories, growth factors, polysaccharides such as fucans, extracellular matrix proteins such as fibronectin, laminin, elastin, glycosaminoglycans or proteoglycans, and mixtures thereof.

In one embodiment of the present disclosure, the implant also includes a bioresorbable film on at least one of its faces. The film can comprise at least collagen. The film can, for example, comprise oxidized collagen, polyethylene glycol and glycerol. Such a film in embodiments has a smooth antiadhesive surface and is particularly suitable for the manufacture of a wall reinforcement implant that also has anti-adhesive properties.

In one embodiment of the present disclosure, the implant is seeded with live cells. Thus, the present disclosure also relates to a tissue engineering support that includes at least one implant as described above. This support can be seeded with live cells.

The present disclosure also relates to the use of an implant or of a support as described above, for culturing live cells.

BRIEF DESCRIPTION OF THE DRAWINGS

The embodiments of the present disclosure will be described more clearly by means of the description which follows and the attached drawings in which.

DETAILED DESCRIPTION

Figure 1:
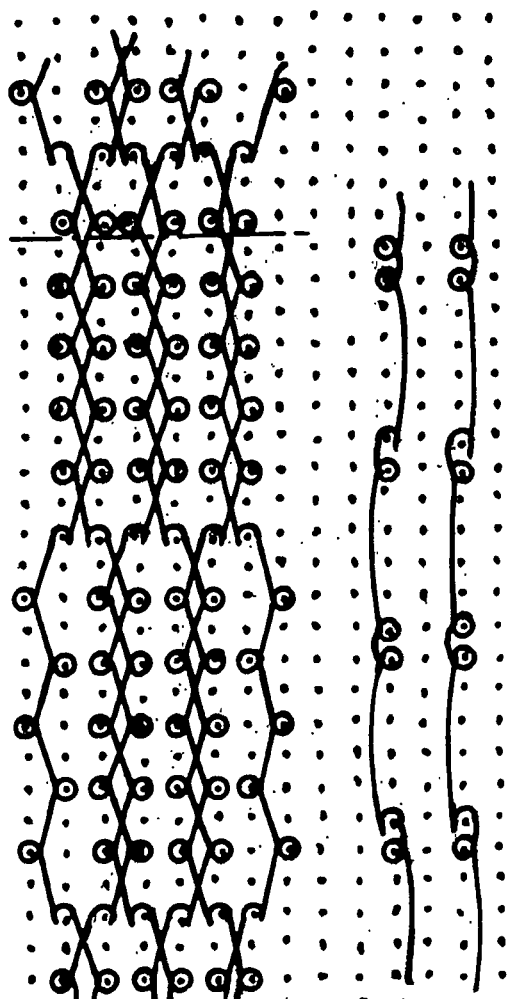
FIGS. 1 to 2B represent patterns of knits suitable for the implant according to the present disclosure.
Figure 1:
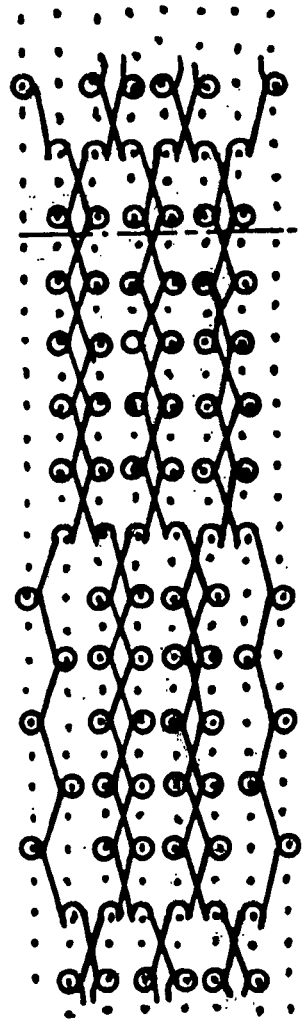

The implant according to the present disclosure includes a porous matrix, which is bioresorbable, based on a collagen sponge which defines first pores. Such a sponge can, in embodiments, be obtained by lyophilization of a collagen suspension. The sponge obtained has pores, or gaps, alveoli, holes or orifices, which may or may not be evenly distributed, and which are more or less interconnected, according to the lyophilization process used. Such lyophilization processes are known. It is known practice to vary the temperature and the rate of freezing and also the characteristics of the collagen solution or suspension to be lyophilized (pH, concentration, etc.) according to the structure of the sponge that it is desired to obtain (see U.S. Pat. No. 4,970,298; Doillon et al, J Biomed Mater Res, 1986; Schoof, J Biomed Mater Res, 2001; O'Brien et al, Biomaterials, 2004).

In embodiments, in the implant according to the present disclosure, the first pores, defined by the sponge, are homogeneously distributed within the matrix. These first pores can, for example, have an average diameter ranging from 50 to 500 µm. These first pores, defined within the sponge taken alone, in the absence of the knit of the implant according to the present disclosure, may or may not be interconnected with one another.

The collagen sponge of the matrix of the implant according to the present disclosure is, in embodiments, obtained from a mixture of at least one collagen which undergoes slow bioresorption in vivo and at least one collagen which undergoes rapid bioresorption in vivo.

The collagen which undergoes slow bioresorption in vivo can be chosen from any collagen, which is pure or derived, which may or may not be heated, and which may or may not be oxidized, having a bioresorption or biodegradation time of between 3 and 12 months. For example, the collagen which undergoes slow bioresorption in vivo can be chosen from glutaraldehyde-crosslinked collagen, bifunctional or trifunctional glycidyl ethers, carbodiimides, acyl azides, divinylsulphone and mixtures thereof. It can also be obtained by crosslinking the collagen by means of physical methods such as photooxidation.

In one embodiment of the present disclosure, glutaraldehyde-crosslinked collagen is used as collagen which undergoes slow bioresorption in vivo. Such a collagen can, for example, be obtained by incubation of a solution of collagen neutralized with a solution of glutaraldehyde, removal of excess glutaraldehyde and neutralization so as to obtain a glutaraldehyde-crosslinked collagen precipitate.

The collagen which undergoes rapid bioresorption in vivo can be chosen from any collagen, which is pure or derived, which may or may not be heated, and which may or may not be oxidized, having a bioresorption or biodegradation time of between one day and 3 months, in embodiments between one day and 8 days. For example, the collagen which undergoes rapid bioresorption in vivo can be chosen from oxidized collagen, glutaraldehyde-crosslinked collagen, bifunctional or trifunctional glycidyl ethers, carbodiimides, acyl azides, divinylsulphone, collagen crosslinked by UV-, beta- or gamma-irradiation or by heat treatment, and mixtures thereof.

In one embodiment of the present disclosure, oxidized collagen, for example oxidized with periodic acid, is used as collagen which undergoes rapid bioresorption in vivo. Examples of preparation of oxidized collagen suitable for the present disclosure are described in patent U.S. Pat. No. 6,596,304.

The collagen used may also be porcine collagen type 1, extracted from porcine dermis by solubilization at acidic pH or by digestion with pepsin, and purified by saline precipitations according to known techniques.

Dry collagen fibres, obtained by precipitation of an acidic solution of collagen by adding NaCl, and then washing and drying of the precipitate obtained with aqueous solutions of acetone having an increasing concentration of from 80% to 100%, are in embodiments used.

Alternatively, bovine or human collagens I or III, or a mixture thereof in any proportions, can be used.

In the case of human collagens of placental origin, they can be prepared by extraction with pepsin according to the method described in application EP-A0 214 035.

The products sold by Inamed Corporation (a wholly-owned subsidiary of Allergan, Inc., Irvine, Calif.), under the names VITROGEN® or ZYDERM®, may also be suitable for the present disclosure.

In one embodiment of the present disclosure, the collagen which forms the sponge is a mixture of oxidized collagen and glutaraldehyde-crosslinked collagen. Thus, a suspension including the oxidized collagen and the glutaraldehyde-crosslinked collagen is prepared. The suspension can include the two collagens in equal concentrations or, on the other hand, predominantly one of the two collagens and a minor amount of the other. The ratio of the concentration of one of the two types of collagen to the other is in embodiments between 1 and 5.

The evolution of the interconnectivity of the implant after it has been implanted in vivo and the associated cell growth in the implant can be controlled by means of the ratio of the concentration of collagen which undergoes slow resorption to the concentration of collagen which undergoes rapid resorption. The evolution of the interconnectivity of the implant after it has been implanted in vivo and the associated cell growth in the implant can also be controlled by means of the nature and the rate of degradation of the collagen which undergoes slow resorption and of the collagen which undergoes rapid resorption.

The evolution of the interconnectivity of the implant after it has been implanted in vivo and the associated cell growth in the implant can also be controlled by means of the nature and the rate of degradation of the collagen which undergoes slow resorption and of the collagen which undergoes rapid resorption and, at the same time, by the ratio of the concentration of collagen which undergoes slow resorption to the concentration of collagen which undergoes rapid resorption.

It is possible to vary the respective concentrations of the collagen which undergoes slow resorption and of the collagen which undergoes rapid resorption in the initial suspension, and therefore in the sponge obtained after lyophilization, according to the manner in which it is desired to bring about an evolution in the degree of interconnectivity in the final implant and, consequently, the cell growth associated therewith. For example, if the intention is for the interconnectivity to increase rapidly within the final implant once it is implanted in vivo, a predominant proportion of collagen which undergoes rapid resorption will be provided in the sponge of the matrix of the implant according to the present disclosure. As this collagen which undergoes rapid resorption degrades, for example in a few days, it will be replaced by gaps which will increase the interconnectivity of the implant and the cell growth will be able to take place rapidly within the numerous spaces left vacant by the degradation of the collagen which undergoes rapid resorption.

It is also possible to vary the rate of degradation of the collagen which undergoes rapid resorption, by changing the nature of the collagen or modifying the degree of oxidation of the oxidized collagen. For example, if the intention is for the interconnectivity to increase rapidly within the final implant once it is implanted in vivo, a collagen which degrades more rapidly, such as a relatively nonoxidized collagen or such as natural collagen, will be provided. The term "natural collagen" is intended to mean a collagen which has not been chemically modified, other than by a possible treatment with pepsin, aimed at eliminating telomeres, therefore reducing its immunogenicity. The expression "collagen which is relatively nonoxidized" is intended to mean a natural collagen oxidized with periodic acid at a concentration of less than $10^{-2}$ M, in embodiments between $10^{-4}$ M and $8 \times 10^{-3}$ M, as described, for example, in French Patent FR 2,601,371.

Conversely, if a less rapid cell growth is desired, a minority proportion of collagen which undergoes rapid resorption will be provided in the sponge of the matrix of the implant according to the present disclosure. It will also be possible to choose a collagen which degrades less rapidly, such as a collagen with a greater degree of oxidation or such as collagen crosslinked with crosslinking agents such as diglycidyl ethers, carbodiimides, acyl azides, divinylsulphone or glutaraldehyde at a low dose, or collagen crosslinked by physical methods (UV, beta-irradiation, gamma-irradiation, photooxidation). The term "collagen with a greater degree of oxidation" is intended to mean a natural collagen oxidized with periodic acid at a concentration of greater than $10^{-2}$ M, in embodiments between $10^{-2}$ M and $10^{-1}$ M, as described by French Patent FR 2,601,371.

The implant according to the present disclosure also includes a porous, bioresorbable, three-dimensional knit which defines second pores. This knit can include only monofilament and/or multifilament yarns made of bioresorbable material. By way of example, the multifilament yarns can have a count ranging from 50 to 110 dtex. Also by way of example, the monofilament yarns can have a diameter ranging from 0.10 to 0.18 mm. In embodiments, the yarns constituting the knit of the implant according to the present disclosure have an in vivo resorption or degradation time ranging from approximately 3 months to 2 years. In fact, in embodiments the knit of the implant according to the present disclosure can be the last element of the implant to resorb completely and to disappear so as to be replaced solely by the regenerated tissue. In fact, the knit of the implant according to the present disclosure provides rigidity and some of the mechanical strength necessary for the implant to perform its reinforcement role.

Thus, the bioresorbable material that constitutes the yarns of the knit of the implant according to the present disclosure may advantageously be chosen from poly(lactic acid) (PLA), poly(glycolic acid) (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof.

In one embodiment of the present disclosure, the three-dimensional knit includes a first face and a second face, opposite and separated from one another by the thickness of the knit. The first and second faces are in embodiments connected to one another by a spacer. For example, the spacer consists of a sheet of linker yarns. Each face can include one or more sheets of yarns. The yarns constituting each of the two faces and the spacer may be identical or different.

In one embodiment of the present disclosure, the first and second faces of the knit are identical. For example, each face includes only of two sheets of yarns. In embodiments, the yarns constituting the two faces of the knit are made of multifilament yarns of poly(lactic acid). Such yarns resorb completely in vivo in the space of 6 months to 2 years. Yarns suitable for producing the two faces of the knit of the implant according to the present disclosure are, for example, 84 dtex poly(lactic acid) multifilament yarns with 24 filaments per yarn, each filament having a diameter of approximately 18 μm. Alternatively, 83.3 dtex poly(glycolic acid) multifilament yarns with 30 filaments per yarn can also be used.

In one embodiment of the present disclosure, the yarns constituting the spacer are monofilament yarns. Such an embodiment makes it possible to confer on the knit a better mechanical strength and a better resistance to thermosetting when the knit is thermoset after the knitting phase. In embodiments, the spacer is made of monofilament yarns of poly(lactic acid). Yarns suitable for preparing the spacer of the knit of the implant according to the present disclosure are, for example, 220 dtex poly(lactic acid) monofilament yarns, the monofilament having a diameter of approximately 150 μm.

Examples of a knit suitable for the implant according to the present disclosure are described in document EP 0 999 805. The knit of the implant according to the present disclosure can be produced on a knitting machine of the Raschel type, for example using 5 or 6 bars.

Figure 2:
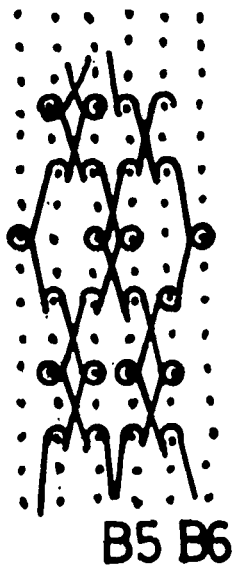
Figure 2:
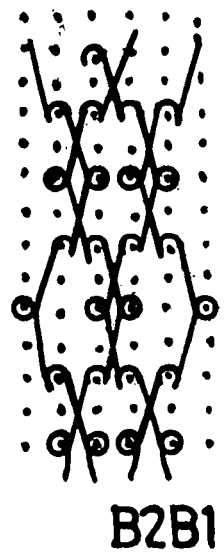

Examples of a pattern suitable for the knit of the implant according to the present disclosure are shown in FIGS. 1 and 2.

In these figures, the references B1-B6 represent the bars 1 to 6.

The first face can, for example, be produced with bars 1 and 2. The second face can be produced in the same way, with bars 5 and 6.

Figure 2A:
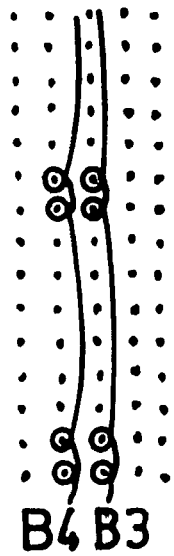
Figure 2B:

The spacer can be produced with bar 3 (cf. FIG. 1) or bars 3 and 4 (FIGS. 2A and 2B).

The knit of the implant according to the present disclosure defines second pores, or alveoli, gaps, holes or orifices. These second pores in embodiments have an average diameter or an average volume ranging from 1 to 5 mm. These second pores are completely interconnected with one another. Thus, the second pores created by the knitting at each face of the knit are connected, via the yarns of the spacer, with the second pores created by the knitting at the spacer. Thus, all the second pores and/or gaps, for instance channels, created by the knitting at each face of the knit and in the thickness of the knit are open, connected to one another and communicate with one another: for example, it is possible for a cell to pass from one pore to the other, over the entire knit of the support according to the present disclosure.

The second pores of the knit of the implant according to the present disclosure define, for the knit, a two-dimensional porosity and a three-dimensional porosity.

In the present application, the two-dimensional porosity is calculated from two-dimensional images corresponding to views from above the implant according to the present disclosure, these images then being processed by software which analyses them, for instance the Image J software. For example, for a measurement, the density of the knit was determined using a Nikon SMZ 800 binocular microscope with a Nikon DN100 digital camera used in combination with a PC computer. The digital images seen from above the knit were multiplied by a factor of 20 and were then processed by the Image J software in order to determine the density of the knit. Once the digital image is captured by the software, it is processed such that the surface area corresponding to the empty spaces in the knit is subtracted from the total surface area of the image. The two-dimensional porosity is determined as being the percentage corresponding to the rest of the digital image.

In one embodiment, the knit of the implant according to the present disclosure has a two-dimensional porosity, measured as indicated above, of less than or equal to 20%.

In the present application, the three-dimensional porosity is calculated as follows: the dimensions, i.e. length, width and thickness of the knit, taken alone, are measured; moreover, the density of the yarns used to knit this knit is known. The knit is weighed. The volume occupied by the empty spaces within the knit is deduced therefrom by simple subtraction. The three-dimensional porosity over the knit as a whole is determined as being the percentage of empty volume relative to the total volume of the knit.

In one embodiment, the knit of the implant according to the present disclosure has a three-dimensional porosity, measured as indicated above, of greater than or equal to 90%.

Thus, in embodiments, the knit of the implant according to the present disclosure has both a two-dimensional porosity of less than or equal to 20% and a three-dimensional porosity of greater than or equal to 90%. The combination of these porosity values makes it possible in particular to obtain, with the sponge forming the matrix of the implant according to the present disclosure, an interconnectivity for excellent cell growth in vivo when the implant is used. In fact, during the manufacture of the implant according to the present disclosure, the collagen forming the sponge of the matrix of the implant has, by virtue of the high three-dimensional porosity of the knit of the implant according to the present disclosure, a direct access within the three-dimensional structure and therefore the pores of the knit. Thus, during the manufacture of the implant, and in particular during the lyophilization for obtaining the sponge in which the knit is embedded, as will be explained below, the high porosity of the knit makes it possible to make all the pores, i.e. the first pores due to the sponge and the second pores of the knit, at least partially interconnected with one another.

Furthermore, it is also advantageous for the knit of the implant according to the present disclosure to have a relatively low two-dimensional porosity, in embodiments less than or equal to 20%, in order to maintain in the knit and therefore in the implant according to the present disclosure, mechanical properties that are appropriate for the function that it is called upon to perform, i.e. to reinforce a defective wall, in particular sufficient mechanical strength.

In one embodiment of the implant of the present disclosure, the three-dimensional knit has a thickness ranging from approximately 2 mm to 6 mm, in embodiments ranging from 2 mm to 4 mm.

In one embodiment of the present disclosure, the knit is isoelastic, i.e. it has isotropic elastic mechanical properties, i.e. substantially equivalent in all directions.

Thus, the knit of the implant according to the present disclosure in embodiments has a mechanical strength in the longitudinal direction, i.e. in the direction of the warp of the knit, measured according to ISO standard 13934-1 (properties of substances in tensile testing), ranging from 50 to 300 N. In embodiments, the knit of the implant according to the present disclosure has mechanical strength in the transverse direction, i.e. in the direction of the weft of the knit, measured according to ISO standard 13934-1, ranging from 50 to 300 N.

In embodiments, the knit of the implant according to the present disclosure has a mechanical strength in the longitudinal direction, i.e. in the direction of the warp of the knit, measured according to ISO standard 13934-1, ranging from 100 to 250 N. In embodiments, the knit of the implant according to the present disclosure has a mechanical strength in the transverse direction, i.e. in the direction of the weft of the knit, measured according to ISO standard 13934-1, ranging from 75 to 200 N.

In embodiments, the knit of the implant according to the present disclosure has an elongation at 50N in the longitudinal direction, i.e. in the direction of the warp of the knit, measured according to ISO standard 13934-1, ranging from 10% to 50%. In embodiments, the knit of the implant according to the present disclosure has an elongation at 50N in the transverse direction, i.e. in the direction of the weft of the knit, measured according to ISO standard 13934-1, ranging from 10% to 50%.

In one embodiment, at least part of the yarns constituting the three-dimensional knit are covered with a bioresorbable coating. The bioresorbable coating can be chosen from oxidized collagen, glutaraldehyde-crosslinked collagen, bifunctional or trifunctional glycidyl ethers, carbodiimides, acyl azides, divinyl-sulphone, collagen crosslinked by UV-, beta- or gamma-irradiation or by heat treatment, and mixtures thereof. The assembly of yarns constituting the knit can be covered with such a coating. For example, the coating is made of collagen. In particular, a collagen chosen from oxidized collagen, glutaraldehyde-crosslinked collagen and mixtures thereof can be used for such a coating.

In one embodiment, the yarns of the knit are covered, at least in part by coating the knit in a solution or suspension of collagen, in one step or in several steps. A coating step includes the actual coating of the knit with the collagen and the drying of the knit. The collagen deposited on the yarns can be crosslinked with glutaraldehyde after each application, as many times as the total number of coating cycles. In embodiments, the yarns are covered by carrying out two or three successive coating cycles.

In another embodiment, the bioresorbable coating can be chosen from polysaccharides including hyaluronic acid, alginic acid, polyglucuronic acid, chitosan, starch, soluble cellulose derivatives and mixtures thereof.

In another embodiment, before it is coated with the bioresorbable coating described above, the knit according to the present disclosure can be subjected to a surface treatment in order to render it more hydrophilic and thus promote the deposition of the collagen and/or the polysaccharides mentioned above on the knit.

The surface treatment can be carried out according to any process known to those skilled in the art.

Such a coating makes it possible to reduce the surface of the knit accessible to bacteria and to inflammatory cells. The risks of inflammation and sepsis are thus reduced.

In one embodiment of the present disclosure, the implant also includes one or more biological active agents that promote tissue regeneration, chosen, inter alia, from antiseptic agents, anti-inflammatory agents, growth factors, extracellular matrix proteins such as fibronectin, laminin or elastin, glycosaminoglycans, proteoglycans, and mixtures thereof. This active agent may, for example, be incorporated into the sponge during the manufacture of the implant.

In order to produce the implant according to the present disclosure, the knit as described above is knitted, beforehand, on a knitting machine. This knit is, in embodiments, thermoset, for example by being placed in an oven at from 100 to 200° C., for 30 seconds to 5 minutes, depending on the chemical nature of the yarns used. The knit is then cut to the sizes desired for the implant. The thermosetting can also be carried out after the knit has been cut up.

A suspension including the collagen intended to form the sponge of the matrix is then prepared. For example, this suspension includes a mixture of collagen which undergoes rapid resorption and collagen which undergoes slow resorption. The collagen suspension is then poured over the three-dimensional knit so as to completely cover it. The whole is then lyophilized, for example according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. The vacuum at the end of secondary desiccation is in embodiments between 0.005 and 0.2 mbar. The total lyophilization time is from 18 to 72 hours.

The lyophilization makes it possible to obtain an implant in which all the pores, i.e. the first pores, formed with the sponge, and the second pores, i.e. those of the three-dimensional knit present prior to the lyophilization, are at least partially interconnected.

The implant according to the present disclosure can also be coated, on at least one of its faces, with a bioresorbable film. This film is in embodiments smooth at the surface and can be used for the prevention of post-surgical adhesions.

Such a film may be a collagen film. In one embodiment of the present disclosure, such a film includes oxidized collagen, polyethylene glycol and glycerol.

This bioresorbable film can be applied to one face of the implant according to the present disclosure in the following way: a solution, for example of oxidized collagen, polyethylene glycol and glycerol, is prepared and then spread out in order to form a thin sheet on a hydrophobic flat support, for example on a support of polyvinyl chloride or polystyrene. The face of the implant to be coated can then be applied carefully to the collagen gel. After exposure to ambient temperature and evaporation, a film which coats one face of the implant is obtained. It is also possible to coat the two faces of the implant with such a film. This film in embodiments resorbs rapidly in vivo, for example in less than 8 days.

Thus, the implant according to the present disclosure is entirely bioresorbable in vivo. As a result, it is particularly suitable for treatments, for example for wall defects, which do not require a permanent reinforcement. By virtue of the gradual degradation of the various elements of the implant, for example, firstly, the part of the sponge corresponding to the collagen which undergoes rapid resorption, then, secondly, the part of the sponge corresponding to the collagen which undergoes slow resorption, and then finally, thirdly, the knit, the degree of interconnectivity of the implant evolves, leaving more and more space for cell growth, which occurs gradually, while, throughout this period of time, the implant maintains the mechanical properties necessary for it to function. The more the mechanical strength of the implant decreases due to the degradation of the elements of which it is made up, the more the intrinsic strength of the treated wall increases due to the presence of regenerated tissue, this regenerated tissue invading and trapping little by little the remainder of the implant until the latter is completely resorbed.

The implant according to the present disclosure can also be used in vitro as a tissue engineering support for cell culture. Thus, it is possible to seed the implant according to the present disclosure with live cells. Such live cells, cultured within the implant according to the present disclosure, can release growth factors and extracellular matrix, which can assist in the repair and/or strengthening of soft tissues. Thus, it is possible to provide the implant according to the present disclosure, in vitro, with cells that promote tissue repair, and then to subsequently implant the support into the wall of the soft tissue to be strengthened. The repair can be thus accelerated in vivo due to the presence of cells promoting regeneration as soon as the implant is implanted.

The implant according to the present disclosure can be seeded with cells chosen from the following cells, alone or in any possible combinations thereof: striated muscle cells, smooth muscle cells, endothelial cells, epithelial cells, mesothelial cells, fibroblasts, myofibroblasts, and stem cells of each of the above cell types.

For example, it is possible to seed the implant described above with striated or smooth muscle cells, with their progenitors, and fibroblasts, in order to obtain effective wall repair.

Moreover, it is also possible to use an implant as described above, one face of which is coated with a bioresorbable film: for example, muscle cells can be cultured within the sponge of the matrix of the implant, while endothelial or epithelial cells are cultured on the bioresorbable film. These endothelial or epithelial cells, after implantation of the implant, make it possible to accelerate the formation of a new endothelium or epithelium in vivo.

Similarly, it is possible to carry out effective reconstruction of an abdominal wall by seeding, before implantation, an implant according to the present disclosure with mesothelial cells on the film and with striated muscle cells in the sponge.

Similarly, it is possible to carry out effective reconstruction of a bladder by seeding, before implantation, an implant according to the present disclosure with urothelial cells on the film and with smooth muscle cells in the sponge.

The present disclosure also relates to a method for repairing a wall defect, characterized in that it includes the step consisting in implanting at the site of the wall defect a seeded or unseeded implant as described above.

The non-limiting examples which follow illustrate embodiments of the present disclosure.

EXAMPLES

Example 1

Preparation of a Knit for the Implant

A three-dimensional knit is produced on a double needle-bar Raschel knitting machine, with 5 guide bars. Each of the faces of the knit, i.e. the first face and the second face, is produced with two guide bars. With reference to FIG. 1, the first face is produced with bars B1 and B2, and the second, opposite, face is produced with bars B5 and B6, each bar being threaded one full, one empty, with the following respective charts:

Bar B1: 1-0-1-1/1-2-2-2/2-3-2-2/2-1-2-2/2-3-2-2/2-1-2-2/ 2-3-2-2/2-1-1-1/1-0-1-1/1-2-1-1/1-0-1-1/1-2-1-1//.

Bar B2: 2-3-2-2/2-1-1-1/1-0-1-1/1-2-1-1/1-0-1-1/1-2-1-1/ 1-0-1-1/1-2-2-2/2-3-2-2/2-1-2-2/2-3-2-2/2-1-2-2//.

Bar B5: 2-2-2-1/1-1-1-0/1-1-1-2/1-1-1-0/1-1-1-2/1-1-1-0/ 1-1-1-2/2-2-2-3/2-2-2-1/2-2-2-3/2-2-2-1/2-2-2-3//.

Bar B6: 1-1-1-2/2-2-2-3/2-2-2-1/2-2-2-3/2-2-2-1/2-2-2-3/ 2-2-2-1/1-1-1-0/1-1-1-2/1-1-1-0/1-1-1-2/1-1-1-0//.

The pattern corresponding to bars 1, 2, 5 and 6 is reproduced in FIG. 1. Such threading and such a pattern result in porous faces. It is possible to adapt the pattern so as to have alveoli or pores on each face, opposite one another or shifted with respect to one another, in order to make the three-dimensional knit more or less transparent.

Bars B1-B2 and B5-B6 which produce the first and second faces of the knit are threaded with 83.3*/24° multifilament yarns (decitex count: 83.3 g per 10 000 m of yarn) of poly (lactic acid). The filament diameter of the multifilament yarns is approximately 18 μm.

Figure 3:
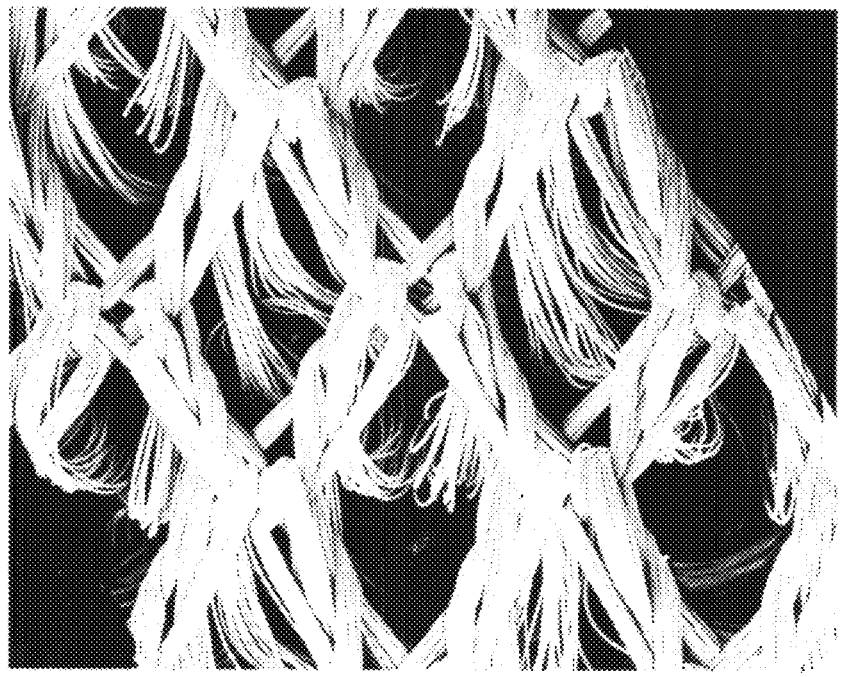
FIGS. 3 and 4 represent scanning electron microscopy images (Hitachi S800 microscope with image acquisition and analysis system) of a knit of an implant according to the present disclosure, made with multifilament spacer yarns, respectively from the front and from the side.

FIG. 3 represents a scanning electron microscopy image of one face of such a knit.

With reference to FIG. 1, the spacer is produced using bar B3, threaded one full, one empty, according to the following chart:

Bar B3: 0-0-0-0/0-0-0-0/0-1-0-1/1-1-1-1/1-1-1-1/1-0-1-0/ 1-1-1-1/1-1-1-1/1-0-1-0/0-0-0-0/0-0-0-0/0-1-0-1//.

Bar B3 is threaded with 83.3*/24° multifilament yarns (decitex count: 83.3 g per 10 000 m of yarn) of poly(lactic acid).

The pattern used for the knitting is reproduced in FIG. 1.

Figure 4:

FIG. 4 represents a scanning electron microscopy image of the spacer of such a knit.

The knit is cleaned with methanol-ether and is sterilized by gamma-irradiation.

The knit is thermoset by placing it in an oven at approximately 90° C. for 1 to 5 min.

Such a knit has the following properties, measured as indicated in the present application:

Weight per surface area (g/m$^2$): 165

Pore size: 2.1 mm×1 mm

Thickness: 2.6 mm

Three-dimensional porosity: 95%

Two-dimensional porosity: 4%

This knit is isoelastic. In particular, it has the following mechanical properties:

| | Property | | | | | |
|---|---|---|---|---|---|---|
| | Str Wa | Str We | El B Wa | El B We | El Wa 50 N | El We 50 N |
| Knit Example 1 | 182 | 123 | 69 | 50 | 20 | 22 |

Str Wa: Mechanical Strength in the direction of the warp (in N); calculated according to ISO standard 13934-1
Str We: Mechanical Strength in the direction of the weft (in N); calculated according to ISO standard 13934-1;
El B Wa: Elongation at break in the direction of the warp (as %) calculated according to ISO standard 13934-1;
El B We: Elongation at break in the direction of the weft (as %) calculated according to ISO standard 13934-1;
El Wa 50 N: Elongation at 50 N in the direction of the warp (as %) calculated according to ISO standard 13934-1;
El We 50 N: Elongation at 50 N in the direction of the weft (as %) calculated according to ISO standard 13934-1.

Example 2

Preparation of a Knit for the Implant

A knit is prepared in the same way as in Example 1, in which the multifilament yarns of the spacer are replaced with 220 dtex monofilament yarns of poly(lactic acid), with a diameter of approximately 150 µm.

Figure 5:
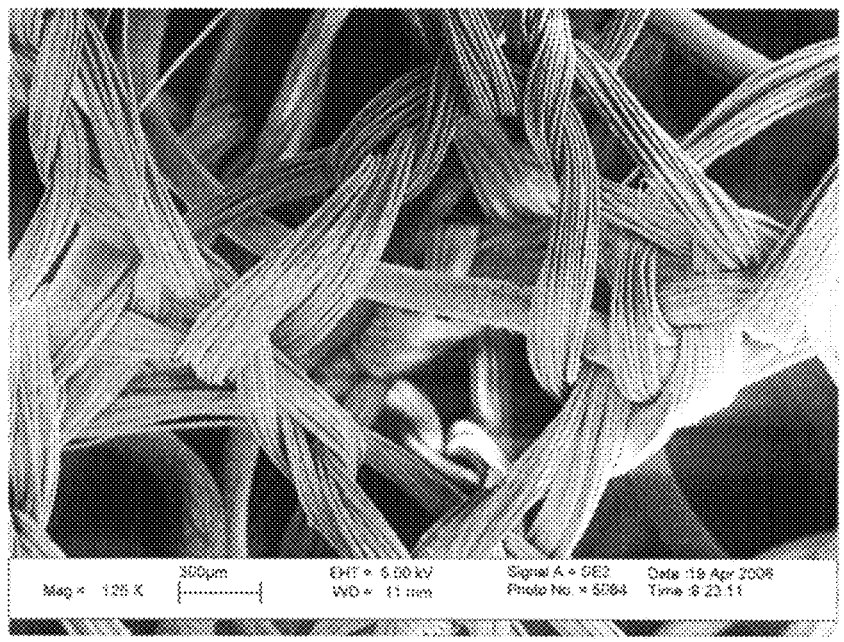
FIG. 5 represents a scanning electron microscopy image (Hitachi S800 microscope with image acquisition and analysis system) of a knit of an implant according to the present disclosure, made with monofilament spacer yarns.

FIG. 5 represents a scanning electron microscopy image of the spacer of such a knit, prepared with such monofilament yarns.

Such a knit has the following properties, measured as indicated in the present application:
Weight per surface area (g/m$^2$): 104
Pore size: 1.9 mm×1.4 mm
Thickness: 3.3 mm
Three-dimensional porosity: 97.5%
Two-dimensional porosity: 20%

This knit is isoelastic. In particular, it has the following mechanical properties:

| | Property | | | | | |
|---|---|---|---|---|---|---|
| | Str Wa | Str We | El B Wa | El B We | El Wa 50 N | El We 50 N |
| Knit Example 2 | 193 | 82 | 44 | 90 | 11 | 45 |

Str Wa: Mechanical Strength in the direction of the warp (in N); calculated according to ISO standard 13934-1
Str We: Mechanical Strength in the direction of the weft (in N); calculated according to ISO standard 13934-1;
El B Wa: Elongation at break in the direction of the warp (as %) calculated according to ISO standard 13934-1;
El B We: Elongation at break in the direction of the weft (as %) calculated according to ISO standard 13934-1;
El Wa 50 N: Elongation at 50 N in the direction of the warp (as %) calculated according to ISO standard 13934-1;
El We 50 N: Elongation at 50 N in the direction of the weft (as %) calculated according to ISO standard 13934-1.

Example 3

Preparation of a Knit for the Implant

A three-dimensional knit is prepared on a double needlebar Raschel knitting machine, with 6 guide bars. Each of the faces of the knit, i.e. the first face and the second face, is prepared with two guide bars. With reference to FIG. 2, the first face is prepared with bars B1 and B2, and the second, opposite, face is prepared with bars B5 and B6, each bar being threaded one full, one empty, with the following respective charts:
Bar B1: 1-0-1-1/1-2-2-2/2-3-2-2/2-1-1-1//.
Bar B2: 2-3-2-2/2-1-1-1/1-0-1-1/1-2-2-2//.
Bar B5: 2-2-2-1/1-1-1-0/1-1-1-2/2-2-2-3//.
Bar B6: 1-1-1-2/2-2-2-3/2-2-2-1/1-1-1-0//.

The pattern corresponding to bars 1, 2, 5 and 6 is reproduced in FIG. 2. Such threading and such a pattern result in porous faces. In this example, the gaps or pores on each face have the following values:
Width: approximately 1 to 1.3 mm
Height: 1.1 to 1.4 mm.

Bars B1-B2 and B5-B6 which produce the first and second faces of the knit are threaded with poly(lactic acid) 83.3 dtex multifilament yarns.

With reference to FIG. 2A, the spacer is prepared using bars B3 and B4, threaded one full, one empty, according to the following respective charts:
Bar B3: 0-1-0-1/0-0-0-0/0-0-0-0/0-0-0-0//.
Bar B4: 0-0-0-0/0-0-0-0/0-1-0-1/0-0-0-0//.

Alternatively, with reference to FIG. 2B, bars B3 and B4 are threaded one full, one empty, according to the following respective charts:
Bar B3: 0-1-0-1/0-0-0-0/0-0-0-0/0-0-0-0//.
Bar B4: 0-1-0-1/0-0-0-0/0-0-0-0/0-0-0-0//.

The patterns used for the knitting are respectively reproduced in FIGS. 2A and 2B. Bars 3 and 4 are complementary. One of bars 3 and 4, for example bar B3, is threaded with monofilament yarns, for example 220 dtex poly(lactic acid), so as to give thickness and resilience to the three-dimensional knit. The other bar, for example bar B4, is threaded with multifilament yarns, for example 83.3 dtex poly(lactic acid), so as to give greater opacity between the faces: this opacity is due to the opening of the strands or filaments of the multifilament yarns in the spacer which creates a considerable visual filling coefficient.

Bars B3 and B4 can have an identical displacement and mesh at the same time, as represented in FIG. 2A, or, on the contrary, mesh shifted according to an alternative displacement as shown in FIG. 2B.

The knit is cleaned with methanol-ether and is sterilized by gamma-irradiation.

The knit is thermoset by placing it in an oven at approximately 90° C. for 1 to 5 min.

Example 4

Coating of the Knits of Examples 1 to 3

The knit obtained in Example 1, 2 or 3 is coated in a solution of porcine collagen at 0.8 w/v, by soaking it in the solution, spin-drying it and leaving it to dry under a laminar flow. This cycle of processes is repeated up to two times in order to obtain covering of the yarns.

The collagen used is porcine collagen type I, extracted from porcine dermis by solubilization at acidic pH or by digestion with pepsin, and purified by saline precipitations according to known techniques.

Dry collagen fibres obtained by precipitation of an acid solution of collagen by adding NaCl, and then washing and drying of the precipitate obtained with aqueous solutions of acetone having an increasing concentration of 80% to 100%, are used.

At the end of the coating, the collagen deposited on the knit is crosslinked with glutaraldehyde at 0.5% w/v (aqueous solution of glutaraldehyde at 25%, w/v, sold by Fluka, AG, Buchs, Switzerland), at neutral pH (pH between 6.5 and 7.5), for 2 hours, and is then reduced with sodium borohydride. The reagents used are removed by washing the knit with several water baths.

The crosslinking of the collagen deposited on the knit can alternatively be carried out at the end of each coating cycle.

Figure 6:
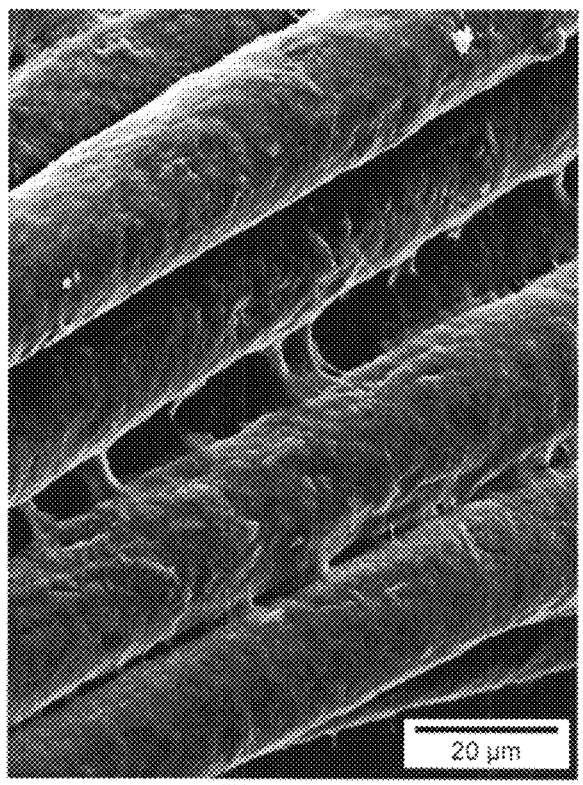
FIG. 6 is a scanning electron microscopy image (Hitachi S800 microscope with image acquisition and analysis system) of a coated knit suitable for the implant according to the present disclosure.

FIG. 6 is a scanning electron microscopy image of the coated knit obtained in Example 1.

Preparation of Glutaraldehyde-Crosslinked Collagen

Porcine collagen is solubilized in water at a final concentration of 1% w/v.

The collagen used is porcine collagen type I, extracted from porcine dermis by solubilization at acidic pH or by digestion with pepsin, and purified by saline precipitations according to known techniques.

Dry collagen fibres obtained by precipitation of an acid solution of collagen by adding NaCl, and then washing and drying the precipitate obtained with aqueous solutions of acetone having an increasing concentration of 80% to 100%, are used.

The solution of collagen at 1% w/v is then neutralized by adding sodium phosphate at a final concentration of 20 mM. The final pH of the suspension was measured at between 6.5 and 7.5.

Glutaraldehyde (aqueous solution of glutaraldehyde at 25%, w/v, sold by Fluka, AG, Buchs, Switzerland) is then added to the suspension at a final concentration of 0.5% w/v. After two hours at ambient temperature, collagen fibres are recovered by filtration of the suspension through a nylon mesh. These fibres are then treated with sodium borohydride for at least two hours until the yellow coloration of the fibres has completely disappeared. The white fibres thus obtained are washed and neutralized at pH 6.5-7.5, and dried by removing the water with acetone. The acetone residues are then evaporated off.

Preparation of Oxidized Collagen

A solution of porcine collagen at 3% w/v is oxidized with periodic acid at a final concentration of 8 mM, at ambient temperature, according to Example 4 of U.S. Pat. No. 6,596,304.

Preparation of the Implant:

A suspension of collagen is prepared by mixing the glutaraldehyde-crosslinked collagen and the oxidized collagen obtained above, at the following concentrations:

0.5 to 1.5% w/v of glutaraldehyde-crosslinked collagen,
0.2 to 1% w/v of oxidized collagen.

The collagen suspension thus obtained is then poured over the three-dimensional knit above so as to completely cover it and the whole is lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. In embodiments, the vacuum at the end of secondary desiccation is between 0.005 and 0.2 mbar. The total lyophilization time is from 18 to 72 hours.

Figure 7:
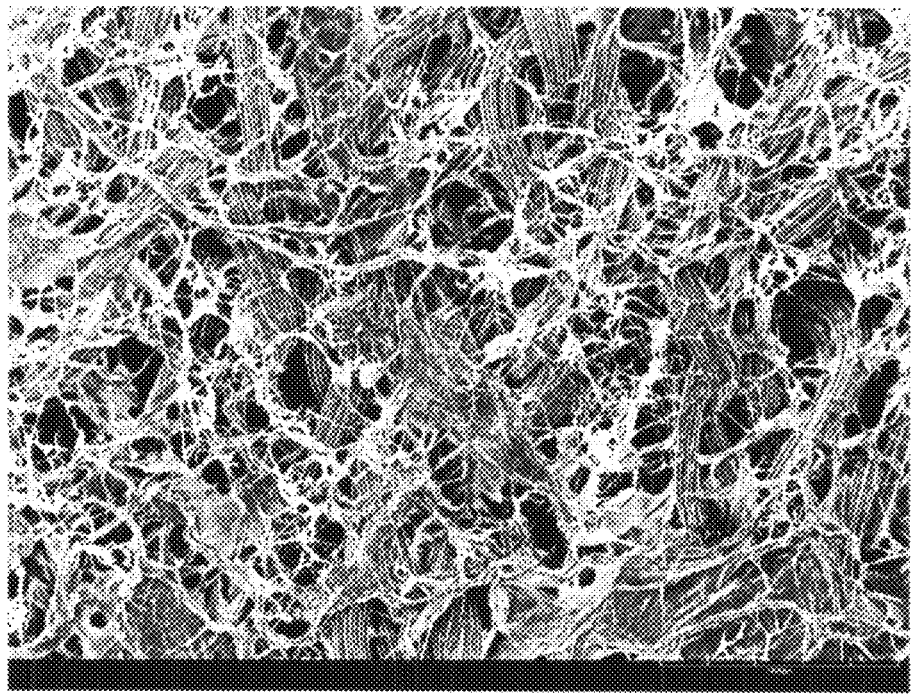
FIG. 7 is a rear view of a scanning electron microscopy image (Hitachi S800 microscope with image acquisition and analysis system) of an implant according to the present disclosure, the three-dimensional knit being filled with the collagen matrix.
Figure 8:
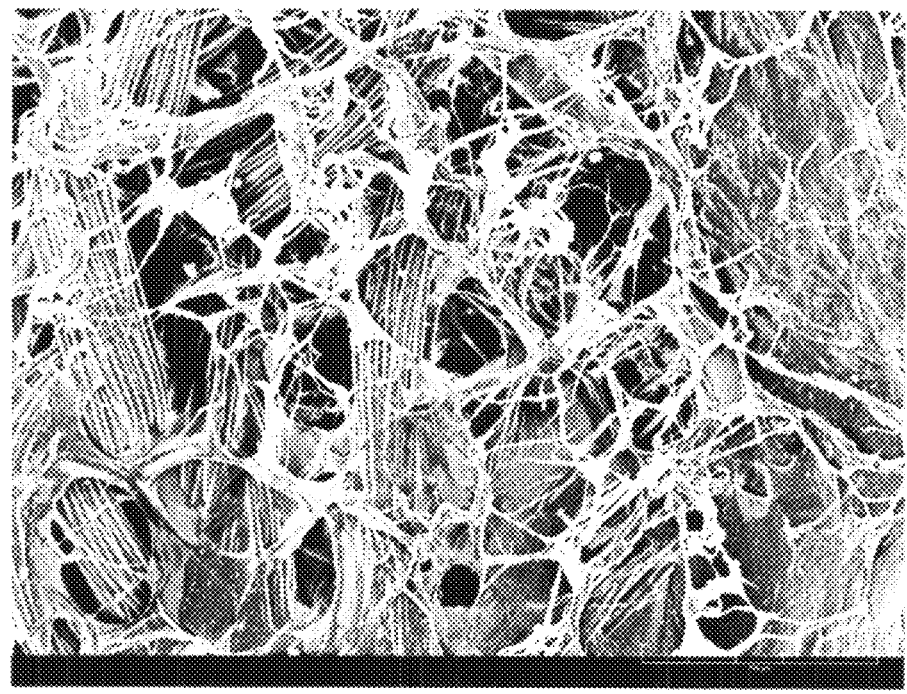
FIG. 8 is a rear view of a scanning electron microscopy image (Hitachi S800 microscope with image acquisition and analysis system) of an implant according to the present disclosure, at a higher magnification than for FIG. 7, the three-dimensional knit being filled with the collagen matrix.

An implant in which all the pores, i.e. those formed with the sponge and those of the three-dimensional knit, are at least partially interconnected, is obtained. Such interconnectivity is visible in the attached figures in which:

FIG. 7 is a rear view of a scanning electron microscopy image of the implant obtained in the present example, with the three-dimensional knit filled with the collagen sponge matrix, FIG. 8 is a rear view, at a higher magnification, of a scanning electron microscopy image of the implant obtained in the present example, with the three-dimensional knit filled with the collagen sponge matrix.

Application of a Film to One Face of the Implant:

The implant obtained above is subsequently coated with an oxidized collagen film as described in Example 2 of U.S. Pat. No. 6,391,939.

A concentrated sterile solution of PEG 4000 (polyethylene glycol having a molecular weight of 4000 D, for example sold by Fluka, AG, Buchs, Switzerland under the trade name PEG 4000) and glycerol is added to a solution of oxidized collagen (obtained by oxidation of porcine collagen) at 3% w/v, so as to obtain a final composition having a PEG 4000 concentration of 1% w/v and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 2.7% w/v, 0.9% w/v and 0.54% w/v, respectively. The solution is then spread out so as to form a thin sheet with a density of 0.133 g/cm$^2$ on a flat hydrophobic support of polyvinyl chloride or polystyrene type. The surface is then exposed to a stream of sterile air at ambient temperature for just under one hour. The implant obtained above is then applied carefully to the gelled sheet of oxidized collagen above. The whole is exposed to a stream of sterile air at ambient temperature until complete evaporation in about 18 hours.

An implant particularly suitable for wall reinforcement and for the prevention of post-surgical adhesions is obtained.

Figure 9:
FIG. 9 is a view of a scanning electron microscopy image (Hitachi S800 microscope with image acquisition and analysis system) of an implant according to the present disclosure coated with a collagen film.

FIG. 9 is a view of a scanning electron microscopy image of the implant described above, coated with the collagen film.

Example 5

Coating of the Knits of Examples 1 to 3

The knits of Examples 1 to 3 are coated with chitosan in a single step. Each knit is coated in a 1% chitosan solution (degree of acetylation: 50%; high molecular weight chitosan, extract of chitosan, Mahtani Chitosan Pvt Ltd), by spraying it with the chitosan solution, until the knit has been completely wetted. Each knit is then dried at +50° C. This cycle of processes is repeated up to four times in order to obtain coating of the yarns.

The invention claimed is:

1. A bioresorbable wall reinforcement implant comprising:
    a bioresorbable porous matrix including a collagen sponge which defines first pores,
    a bioresorbable porous three-dimensional knit which defines second pores,
    said porous matrix filling said three-dimensional knit and all the first and second pores being at least partially interconnected with one another, wherein said collagen comprises a mixture of at least one glutaraldehyde-crosslinked collagen which undergoes slow bioresorption in vivo having a degradation time ranging from approximately 3 months to about 12 months and at least one oxidized collagen which undergoes rapid bioresorption in vivo having a degradation time of up to approximately 8 weeks, wherein a concentration of the at least one glutaraldehyde-crosslinked collagen and the at least one oxidized collagen is provided at a ratio between 1:5 and 5:1.

2. An implant according to claim 1 wherein said three-dimensional knit consists of monofilament and/or multifilament yarns made of bioresorbable material which has an in vivo degradation time ranging from approximately 3 months to 2years.

3. An implant according to claim 2 wherein said bioresorbable material is selected from the group consisting of poly (lactic acid) (PLA), poly(glycolic acid) (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof.

4. An implant according to claim 1 wherein said second pores have an average diameter ranging from 1 to 5 mm.

5. An implant according to claim 1 wherein said knit has a two-dimensional porosity of less than or equal to 20%.

6. An implant according to claim 1 wherein said knit has a three-dimensional porosity of greater than or equal to 90%.

7. An implant according to claim 1 wherein said three-dimensional knit has a thickness ranging from approximately 2 mm to 6 mm.

8. An implant according to claim 1 wherein said three-dimensional knit comprises a first face and a second face, said first face and said second face being opposite and separated from one another by the thickness of said knit, said first face and said second face being connected to one another by a spacer made of monofilament yarns, multifilament yarns or a combination of monofilament yarns and multifilament yarns.

9. An implant according to claim 8 wherein said spacer is made of monofilament yarns.

10. An implant according to claim 8 or 9 wherein said first and second faces of the knit are made of monofilament yarns, multifilament yarns or a combination of monofilament and multifilament yarns.

11. An implant according to claim 8 wherein the monofilament or multifilament yarns used to prepare the first and second faces and the spacer of the three-dimensional knit are selected from the group consisting of yarns made of material which undergoes slow bioresorption, yarns made of material which undergoes rapid bioresorption, and mixtures thereof.

12. An implant according to claim 11 wherein the yarns made of material which undergoes slow bioresorption are made of poly(lactic acid).

13. An implant according to claim 11, wherein the yarns made of material which undergoes rapid bioresorption are selected from the group consisting of poly(glycolic acid) yarns, oxidized cellulose yarns, poly(lactic acid) yarns partially degraded by a treatment such as repeat cycles of gamma-irradiation at doses of greater than or equal to 25 kGy, and mixtures thereof.

14. An implant according to claim 9, wherein said monofilament yarns which make up said spacer consist of yarns made of material which undergoes slow bioresorption.

15. An implant according to claim 14 wherein said monofilament yarns which make up said spacer are made of poly(lactic acid).

16. An implant according to claim 11, wherein said first and second faces are made of a mixture of multifilament yarns made of material which undergoes slow bioresorption and of multifilament yarns made of material which undergoes rapid bioresorption.

17. An implant according to claim 8 wherein said first and second faces are made of poly(lactic acid) multifilament yarns.

18. An implant according to claim 1 wherein said knit is isoelastic.

19. An implant according to claim 1 wherein said knit has a mechanical strength in the longitudinal direction, measured according to ISO standard 13934-1, ranging from 50 to 300 N.

20. An implant according to claim 1 wherein said knit has a mechanical strength in the transverse direction, measured according to ISO standard 13934-1, ranging from 50 to 300 N.

21. An implant according to claim 19, wherein said knit has a mechanical strength in the longitudinal direction, measured according to ISO standard 13934-1, ranging from 100 to 250 N.

22. An implant according to claim 20, wherein said knit has a mechanical strength in the transverse direction, measured according to ISO standard 13934-1, ranging from 75 to 200 N.

23. An implant according to claim 1 wherein said knit has an elongation at 50 N in the longitudinal direction, measured according to ISO standard 13934-1, ranging from 10% to 50%.

24. An implant according to claim 1 wherein said knit has an elongation at 50 N in the transverse direction, measured according to ISO standard 13934-1, ranging from 10% to 50%.

25. An implant according to claim 2 wherein at least a part of the yarns constituting said three-dimensional knit are coated with a bioresorbable coating.

26. An implant according to claim 25 wherein said coating comprises a material selected from the group consisting of collagen, chitosan, polysaccharides and mixtures thereof.

27. An implant according to claim 1 further comprising one or more active compounds selected from the group consisting of antiseptics, anti-inflammatories, growth factors, polysaccharides, extracellular matrix proteins, and mixtures thereof.

28. An implant according to claim 1 further comprising a bioresorbable film on at least one face of the implant.

29. An implant according to claim 28 wherein said film comprises at least one collagen.

30. An implant according to claim 29 wherein said film comprises oxidized collagen, polyethylene glycol and glycerol.

31. An implant according to claim 1 further comprising live cells.

32. An implant according to claim 31 wherein the cells are selected from the group consisting of striated muscle cells, smooth muscle cells, endothelial cells, epithelial cells, mesothelial cells, fibroblasts, myofibroblasts, stem cells of striated muscle cells, stem cells of smooth muscle cells, stem cells of endothelial cells, stem cells of epithelial cells, stem cells of mesothelial cells, stem cells of fibroblasts, stem cells of myofibroblasts, and combinations thereof.

33. A tissue engineering support comprising at least one implant according to claim 1.

34. A support according to claim 33 further comprising live cells.

35. A support according to claim 34 wherein the cells are selected from the group consisting of striated muscle cells, smooth muscle cells, endothelial cells, epithelial cells, mesothelial cells, fibroblasts, myofibroblasts, stem cells of striated muscle cells, stem cells of smooth muscle cells, stem cells of endothelial cells, stem cells of epithelial cells, stem cells of mesothelial cells, stem cells of fibroblasts, stem cells of myofibroblasts, and combinations thereof.

36. A method of using an implant for culturing live cells comprising providing an implant according to claim 1 for culturing live cells, and seeding the implant with live cells.

* * * * *